(12) United States Patent
Zoltowski et al.

(10) Patent No.: US 6,716,419 B2
(45) Date of Patent: Apr. 6, 2004

(54) PSEUDOPLASTIC, FILM FORMING COSMETIC COMPOSITIONS

(75) Inventors: Craig Eugene Zoltowski, Baltimore, MD (US); John Michael Gilley, Joppa, MD (US); Alic Anthony Scott, Ellicott City, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 98 days.

(21) Appl. No.: 09/874,857

(22) Filed: Jun. 5, 2001

(65) Prior Publication Data

US 2003/0026816 A1 Feb. 6, 2003

(51) Int. Cl.⁷ .................. A61K 7/025; A61K 7/021; A61K 7/06
(52) U.S. Cl. .................. 424/64; 424/63; 424/70.6; 424/70.7
(58) Field of Search ................ 424/64, 63, 70.6, 424/70.7

(56) References Cited

U.S. PATENT DOCUMENTS

| | | |
|---|---|---|
| 3,639,572 A | 2/1972 | Heinrich et al. |
| 4,423,031 A | 12/1983 | Murui et al. |
| 4,710,374 A | 12/1987 | Grollier et al. |
| 4,988,502 A | 1/1991 | Ounanian et al. |
| 5,362,494 A * | 11/1994 | Zysman et al. |
| 5,389,363 A | 2/1995 | Snyder et al. |
| 5,599,547 A | 2/1997 | Bartholomey et al. |
| 5,614,200 A | 3/1997 | Bartholomey et al. |
| 5,620,693 A | 4/1997 | Piot et al. |
| 5,688,493 A | 11/1997 | Sugawara et al. |
| 5,753,215 A | 5/1998 | Mougin et al. |
| 5,843,407 A | 12/1998 | El-Nokaly et al. |
| 5,990,164 A | 11/1999 | Horrobin et al. |
| 6,060,072 A | 5/2000 | Konik et al. |
| 6,221,369 B1 | 4/2001 | Pool et al. |
| 6,372,842 B1 * | 4/2002 | Grisso et al. |

FOREIGN PATENT DOCUMENTS

| | | |
|---|---|---|
| CA | 2125361 A1 | 9/1994 |
| EP | 0 587 637 B1 | 12/1992 |
| EP | 0 530 084 A1 | 3/1993 |
| EP | 0 577 196 A1 | 8/1993 |
| EP | 0 568 035 A2 | 11/1993 |
| EP | 0 573 229 A2 | 12/1993 |
| EP | 0 819 248 A | 8/1997 |
| JP | 57-158714 Kokai A | 9/1982 |
| JP | 1-250305 Kokai A | 10/1989 |
| JP | 07-048231 A | 2/1995 |
| WO | WO 91/12793 A1 | 9/1991 |
| WO | WO 92/21316 A1 | 12/1992 |
| WO | 0 628 304 A1 | 12/1994 |
| WO | WO 96/33690 A1 | 10/1996 |
| WO | WO 97/01321 A1 | 1/1997 |
| WO | WO 98/18431 A2 | 5/1998 |
| WO | WO 98/23251 A1 | 6/1998 |

* cited by examiner

Primary Examiner—Thurman K. Page
Assistant Examiner—Humera N. Sheikh
(74) Attorney, Agent, or Firm—Kenya T. Pierre; Dara M. Kendall

(57) ABSTRACT

The present invention relates to cosmetic compositions having improved application benefits to keratinous tissue and keratinous fibers wherein said compositions have improved application benefits, while avoiding the negatives associated with compositions currently known in the art. The cosmetic compositions exhibit a turning point stress of from about 650 Pa to about 1500 Pa and a high shear rate slope of less than about 0.5 Pa-s. Applicants have also found that the compositions disclosed herein are also useful for other cosmetic applications that relate to keratinous tissues like skin, e.g., lipsticks, foundations, eyeliners, lipliners, eyeshadows, rouges, etc., where it is desirable to provide a smooth application of a long wearing, film-forming cosmetic product.

19 Claims, 2 Drawing Sheets

PSEUDOPLASTIC, FILM FORMING COSMETIC COMPOSITIONS

TECHNICAL FIELD

Figure 1:
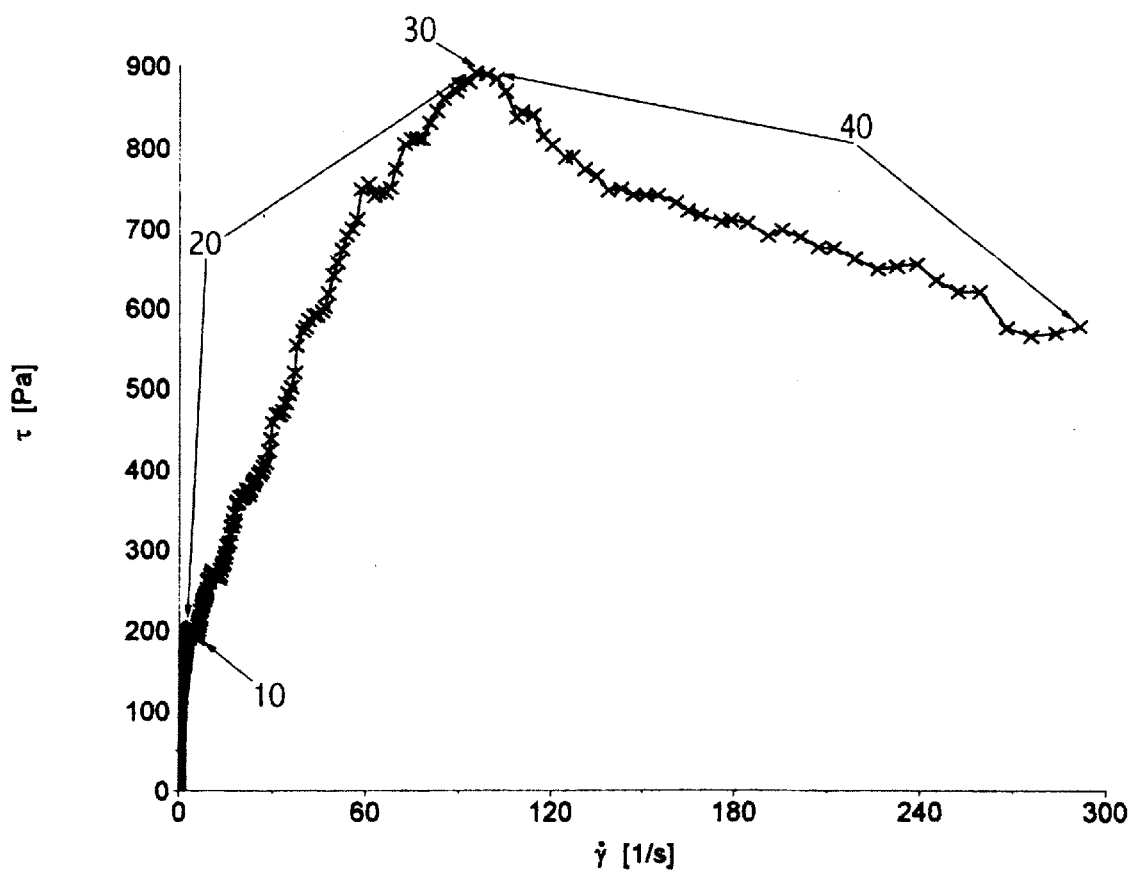

The present invention covers psesudoplastic cosmetic compositions having improved aesthetic attributes such as hair fiber separation, thickening, detangling, smooth application, film-forming properties and improved wear.

BACKGROUND OF THE INVENTION

Mascaras are a major cosmetic product of significant importance to the cosmetic industry. Mascara products are used to enhance the beauty of a person's eyes by coating the eyelashes, and in some cases, the eyebrows, to primarily thicken, lengthen, color, and define the individual lashes.

Mascaras come in a variety of forms including cakes or blocks, creams, gels, and low viscosity liquids. Cake mascaras were originally the most popular form of this cosmetic. They typically contained at least 50% soap whereby the pigment was mixed with the soap and stamped into cakes. With a wet brush, it could be lathered and then applied to the lashes resulting in a satisfactory, smooth application. As such the cream and liquid mascaras have been traditionally limited to relatively low viscosities or have had limited shear-thinning behavior. Their primary drawback was that the film on the lashes was very water soluble and prone to smudging and running of the product transferring to the skin around the perimeter of the eye. Later on, improvements were made to the cake mascara such as incorporating waxes to improve the water-resistance over the original soap-based form. This was usually at the expense of the smoothness of application. That is, as the viscosity of the mascara formulation increases, it becomes increasingly harder to apply, messier, and yields less separation of the lashes.

The advent of mascara applicators also provided a means for expanding formulation options for mascaras. For example, in addition to "cakes", mascaras could be formulated as creams or liquids. Cream mascaras were usually dispersions of waxes and pigments in water with the end consistency very much like a vanishing cream. Combined with an automatic applicator, they soon surpassed the cake mascara in popularity due to their convenience of use. That is, this form became less dependent upon actual technique of the user than the cake-based applicators. Most of the ingredients were similar to the improved form of the cake mascara mentioned above and so many of the same shortcomings were still inherent. However, because it was a cream texture, the concentration of water was greater and allowed for the incorporation of natural and synthetic film-formers to help improve wear. The primary drawback of adding these film-formers was shortened application time. As the water evaporated, the polymers quickly coalesced to form unevenly distributed films, resulting in increased clumping of the mascara on the lashes.

U.S. Pat. No. 5,614,200 discloses the use of a setting rate agent to delay the setting rate of the composition long enough to provide sufficient time to distribute the mascara in semi-liquid form to avoid such clumping. The formulations disclosed therein provided lash separation and application ease at the expense of wear (i.e., smearing and water resistance). There remains, however, a need for cosmetic compositions, particularly mascaras that detangle and separate lashes without sacrificing wear and lash thickening. More importantly, there is a need for cosmetic products, namely mascaras, that exhibit improved application and separation benefits despite being viscous. Notwithstanding the above, the present inventors have found that cosmetic compositions that exhibit certain rheological performance parameters relative to pseudoplasticity are capable of achieving these desirable benefits. Therefore, the present inventors have found that compositions, particularly mascaras, that exhibit a turning point stress of from about 650 Pa to about 1500 Pa and a high shear rate slope of less than about 0.5 Pa-s are capable of achieving these desirable benefits. Applicants have also found that the compositions disclosed herein are also useful for other cosmetic applications that relate to keratinous tissues like skin, e.g., lipsticks, foundations, eyeliners, lipliners, eyeshadows, rouges, etc., where it is desirable to provide a smooth application of a long wearing, film-forming cosmetic product.

SUMMARY OF THE INVENTION

The present invention relates to cosmetic compositions having improved application benefits to keratinous tissue and keratinous fibers wherein said compositions have improved application benefits, while avoiding the negatives associated with compositions currently known in the art. The presently claimed compositions exhibit a turning point stress of from about 650 Pa to about 1500 Pa and a high shear rate slope of less than about 0.5 Pa-s.

DETAILED DESCRIPTION OF THE INVENTION

As used herein, the term "cosmetics" includes make-up and hair care products.

The term "make-up" refers to products that leave color on the face, including on the eyelashes, eyebrows, cheeks, lips, etc.

Hair care products are those used to treat, care for, or somehow impart aesthetically pleasing attributes to mammalian hair fibers. Products contemplated by the phrase "hair care products" include, but are not limited to, hair conditioners, shampoos, detangling sprays and the like.

The term "keratinous tissue," as used herein, refers to keratin-containing layers disposed as the outermost protective covering of mammals (e.g., humans, dogs, cats, etc.) which includes, but is not limited to, skin, lips, hair, toenails, fingernails, cuticles, hooves, etc.

As used herein, the term "keratinous fibers" refers particularly to mammalian (e.g., human or animal) hair such as hair on the head or body, brows and eyelashes.

The term "topical application", as used herein, means to apply or spread the compositions of the present invention onto the surface of the keratinous tissue.

The term "dermatologically-acceptable," as used herein, means that the compositions or components thereof so described are suitable for use in contact with mammalian keratinous tissue without undue toxicity, incompatibility, instability, allergic response, and the like.

The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

Rheology Method

The compositions of the present invention exhibit a turning point stress of from about 650 Pa to about 1500 Pa and a high shear rate slope of less than about 0.5 Pa-s. In more preferred embodiments, the turning point stress is from about 750 Pa to about 1200 Pa, and even more preferably, from about 850 Pa to about 1000 Pa. Additionally, it is preferred that the high shear rate slope be less than about 0.25 Pa-s and even more preferred that it be less than about 0.01 Pa-s.

In order to determine the abovementioned rheological limitations of the presently claimed compositions, the following method was developed. The instrument and accessories used for this method include a rheometer (e.g., Haake RS 150), a 20 mm cone with a 1° angle, a 20 mm plate, a water bath, and a solvent trap. The following conditions should be met as well: 1) controlled shear rate run (log); 2) shear rate=from 0.01 $s^{-1}$, to 300 $s^{-1}$, 3) the number of data points collected=300; 4) the duration of the test=300 seconds, and 5) the water bath is set at 25° C.

The rheometer should be correctly calibrated before measurements are taken. The sample should be close to room temperature (25° C.). The application technique in applying the cosmetics of the present invention can be critical. Since the compositions of the present invention tend to be quite thixotropic, i.e., shear prior to measurement tends to affect the measurement results, it is important to be consistent in application technique and to minimize pre-shear. When applying a sample to the base plate, one should gently scoop out the sample in one motion without significant shear or spreading. The sample should be placed gently on the base plate without compressing and rotating the spatula away from the sample. The sample should be centered on the base plate and laid relatively even across the plate. The sample size should be just sufficient to allow some minor flow of the sample out of the gap once the final position of the cone and plate has been reached (0.052 mm). The sample should be about 1 gram. If too much sample is placed or is not evenly layered, the top plate will compress and shear the sample too much affecting the results. The sample should be fresh (i.e., normal volatility content). Therefore, one should avoid taking samples from the air/cosmetic composition interface of the storage container. Quick drying cosmetic compositions are harder to measure and usually require a solvent trap to accurately measure the fresh film. The correct solvent should be used for the sample (i.e., water, isododecane, etc.) that is the primary solvent (or compatible) in the cosmetic composition sample. Once the measurement position is reached, a small bulge of the sample material will protrude from the gap. This should be removed quickly and gently so as not to disturb the top plate and pre-shear the sample. If the top plate is moved then the run should be aborted. The sample preparation should be very quick to reduce drying of the sample (i.e., less than 20 seconds).

Figure 2:
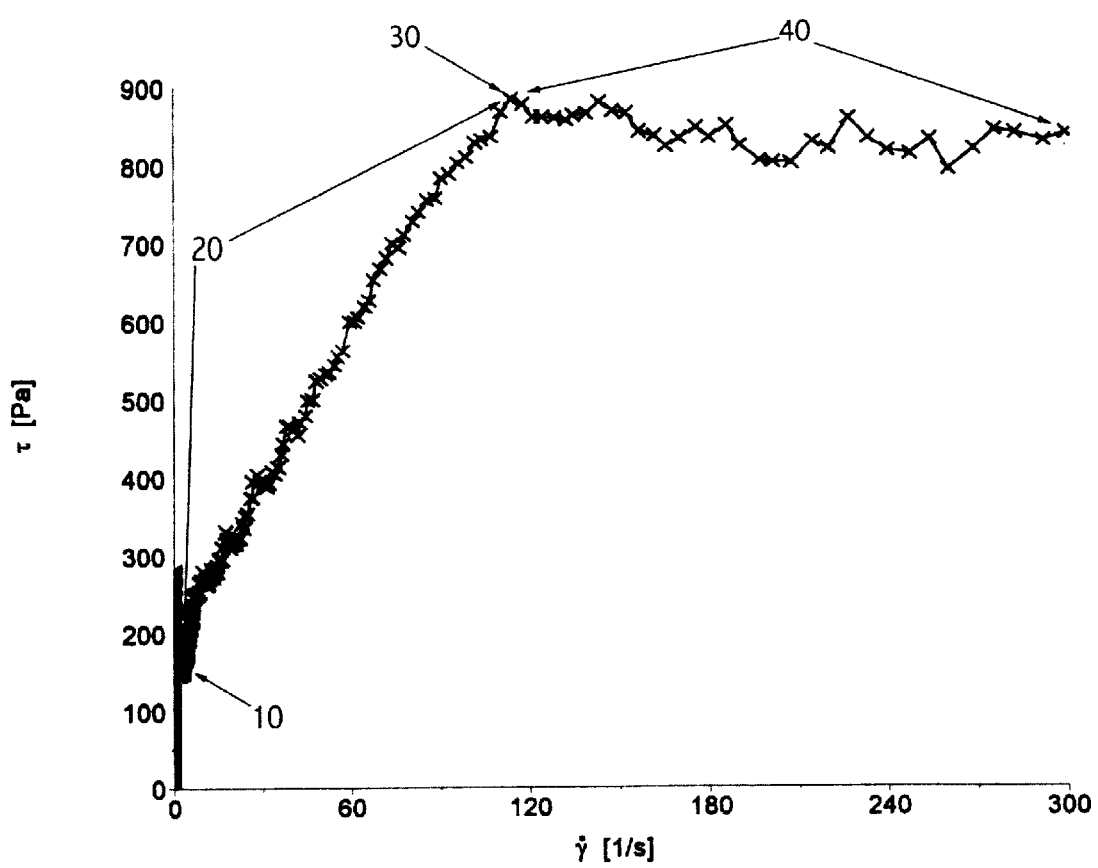

The output of the abovementioned method is plotted with stress ($\tau$ in Pascals) as a function of shear rate ($\dot{\gamma}$ in $s^{-1}$) as shown in FIGS. 1 and 2. In both FIGS. 1 and 2, 10 represents the initial yield, which is the point at which flow or deformation begins. The stress at this point is referred to as the initial yield stress. The low shear rate region 20 is the region where the sample begins to flow yet it also represents the area before which the sample completely shear thins. The slope of the line illustrated by 20 is referred to as the low shear rate slope (measured in Pa-s) and is calculated as the ratio of shear stress/shear rate. 30 represents the turning point. This is the point at which the viscosity of the sample significantly drops, i.e., the sample shear-thins. The shear rate at the turning point is referred to as the turning point shear rate, and the stress at the turning point is referred to as the turning point stress. The high shear rate region 40 is the region after the turning point, when the sample shear thins or flows more easily and more fluid-like. The slope of the line illustrated by 40 is referred to as the high shear rate slope (measured in Pa-s), and is calculated as the ratio of shear stress/shear rate. The turning point can also be described in terms of shear rate rather than stress (one is dependent on the other). It has been found that turning point shear rates from about 85 $s^{-1}$ to about 225 $s^{-1}$, and more preferably, from about 110 $s^{-1}$ to about 175 $s^{-1}$, exhibit similar benefits as the abovementioned turning point stress range.

FIG. 1 demonstrates output from a test sample of the presently claimed compositions. This sample is extremely shear-thinning after the turning point. FIG. 1 indicates that a maximum stress is located at the turning point. This maximum stress at the turning point or negative slope of the high shear rate region represents a material property of the claimed composition. FIG. 2 also illustrates shear-thinning behavior, but in this instance the maximum stress plateaus. Some embodiments of the present invention may even increase slightly in slope, but should be less than about 0.5 Pa-s in which case the sample is still quite shear-thinning. It has been found that this shear-thinning behavior (as exemplified in FIGS. 1 and 2) is a major contributor to the consumer benefits that are deemed desirable as mentioned herein.

The test method should be run repeatedly (e.g., 10 times in a row) and the results should yield a relative standard deviation of less than 10% and more preferably less than 5%.

Optional Ingredients

The compositions of the present invention may contain a variety of other components such as are conventionally used in a given product type provided that they do not unacceptably alter the benefits (i.e., the rheological performance limitations) of the invention. These optional components should be suitable for application to mammalian skin, that is, when incorporated into the compositions they are suitable for use in contact with human skin without undue toxicity, incompatibility, instability, allergic response, and the like, within the scope of sound medical or formulator's judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention.

In the present invention numerous optional ingredients may be added to provide additional benefits other than that attributed to the invention as defined above. For example, it is preferred that compositions of the present invention contain a preservative system to inhibit microbiological growth and maintain the integrity of the product. In the present invention, the preservative system does not have a detrimental effect on the composition.

Any optional ingredients known to those skilled in the art may also be used in the invention. Examples of optional ingredients are cosmetic fillers including, but not limited to, mica, talc, nylon, polyethylene, silica, polymethacrylate, kaolin, and Teflon. Suitable cosmetic preservatives including, but not limited to, methylparaben, propylparaben, butylparaben, ethylparaben, potassium sorbate, trisodium EDTA, phenoxyethanol, ethyl alcohol, benzyl alcohol, diazolidinyl urea, imidazolidinyl urea, and quaternium-15 may also be included. Film-forming agents can also be used. Suitable agents include, but are not limited to, natural and synthetic additional film-forming agents such as shellac, acacia, hydroxyethylcellulose, PVP/DMEA, silicone latexes, and polyquaternium-10.

Emulsifiers may also be used to assist in the stabilization of the compositions. These emulsifiers include, but, are not necessarily limited to soaps, phosphate esters, ethoxylated alcohols, ethoxylated fatty acids, ethoxylated fatty esters, polyol ether esters, glycerol esters, sucrose or sorbitan esters, glucose esters, potassium or DEA-cetyl phosphate, triethanolamine, fatty esters, and mixtures thereof.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Suitable optional ingredients are detailed below.

Phospholipid

The compositions of the present invention may comprise at least one phospholipid that has the formula

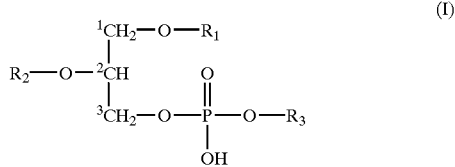

(I)

The nomenclature of phospholipid (I) and the numbering of the C atoms are based on the recommendations (sn-nomenclature, stereospecific numbering) provided in Eur. J. of Biochem. 79, 11–21 (1977) "Nomenclature of Lipids" by the IUPAC-IUB Commission on Biochemical Nomenclature (CBN).

$R_1$ and $R_2$ with the meaning of $C_{10-20}$ acyl can be straight-chain $C_{10-20}$ alkanoyl with an even number of C atoms and straight-chain $C_{10-20}$ alkenoyl with a double bond and an even number of C atoms.

Straight-chain $C_{10-20}$ alkanoyl $R_1$ and $R_2$ with an even number of C atoms are, for example, n-dodecanoyl, n-tetradecanoyl, n-hexadecanoyl or n-octadecanoyl.

Straight-chain $C_{10-20}$ alkenoyl $R_1$ and $R_2$ with a double bond and an even number of C atoms are, for example, 6-cis- or 6-trans-, 9-cis- or 9-trans-dodecenoyl, -tetradecenoyol, -hexadecenoyl, octadecenoyl or -icosenoyl, especially 9-cis-octadecenoyl (oloeyl), also 9,12-cis-octadecadienoyl or 9,12,15-cis-octadecatrienoyl.

A phospholipid (I) in which $R_3$ means 2-trimethylamino-1-ethyl is commonly referred to as lecithin, and a phospholipid (I) in which $R_3$ means 2-amino-1-ethyl is commonly referred to as kephalin. For example, naturally occurring kephalin or lecithin, e.g., kephalin or lecithin from soybeans or hens' eggs, with different or identical acyl groups $R_1$ and $R_2$ or mixtures thereof, are preferred for use herein.

The term "naturally occurring" phospholipid (I) defines phospholipids that do not have a uniform composition in terms of $R_1$ and $R_2$. Therefore, the acyl groups $R_1$ and $R_2$ of naturally occurring phospholipids (e.g., natural lecithins and kephalins) cannot be defined structurally and are derived from naturally occurring fatty acid mixtures.

Specifically, naturally occurring lecithin is defined as a mixture of phosphatides or phospholipid compounds derived from natural sources such as soybeans. The three major phosphatides are phosphatidyl choline, phosphatidyl ethanolamine, and phosphatidyl inositol. A lecithin useful in one embodiment of the present invention is selected from the group consisting of lecithin, concentrated fractions of lecithin, hydrogenated lecithins, and mixtures thereof. Optionally, the lecithin has a phospholipid content of not less than 75% and with less than 5% free oil present, the lecithin can also be oil-free. Examples of these are Centrolex F from Central Soya and the Phospholipon® Series (50G, 80, 90, 100, etc.) from Nattermann Phospholipid. The composition of the lecithin in the present invention can contain about 23% phosphatidyl choline, 20% phosphatidyl ethanolamine, and about 14% phosphatidyl inositol. The remainder of the lecithin is composed of other phospholipids, lipids, carbohydrates, triglycerides, and moisture.

The composition of fractionated lecithins in the present invention are composed primarily of phosphatidyl choline either with a normal fatty acid distribution as occurs naturally in lecithin or through a hydrogenation process whereby the fatty acids consist primarily of saturated types such as stearic and palmitic. Phopholipon 80®, which is mentioned in the present invention, is composed of 76% phosphatidyl choline, 3% lyso phosphatidyl choline, 8% phosphatidic acid, 4% phosphatidyl ethanolamine, and 9% other lipids. Phospholipon 50 or 50G®, which are also mentioned in the present invention, are similar to Phospholipon 80® but are less concentrated in phosphatidyl choline which represents 50% of the mixture. Phosphatidyl ethanolamine is present at 30% along with other components. Other fractionated lecithins include, but are not limited to, Phospholipon 100®, Phospholipon 90H®, Phospholipon 90/906®, and other commercially available fractionated lecithins.

The phospholipid (I) can also be of synthetic origin. Phospholipids that have a uniform composition relative to $R_1$ and $R_2$ are defined by the term synthetic phospholipid. Such synthetic phospholipids can be lecithins and kephalins that are defined above and their acyl groups $R_1$ and $R_2$ have a defined structure and are derived from a defined fatty acid with a degree of purity of greater than about 95%. $R_1$ and $R_2$ can be the same or different and unsaturated or saturated. In one embodiment, $R_1$ is saturated, e.g., n-hexadecanoyl, and $R_2$ is unsaturated, e.g., 9-cis-octadecenoyl (oleoyl). Examples of suitable synthetic phospholipids can be found in U.S. Pat. No. 5,997,888 to Weder et al., issued Dec. 7, 1999.

In a preferred embodiment, the phospholipid is substantially chemically free (e.g., unbound and/or unhindered). "Chemically free" is hereinafter alternatively referred to as "uncomplexed". The phospholipids of the present invention are, therefore, essentially uncomplexed. Moreover, if the composition contains phospholipids in complexed form, such complexing is preferably substantially reversible. This reversibility can be readily determined by one having ordinary skill in the art.

In one embodiment, the composition comprises from about 0.1% to about 5%, more preferably, from about 0.25% to about 4%, and most preferably, from about 0.5% to about 3%, by weight of the composition, of the phospholipid.

PVP-copolymer

PVP-copolymers may also be incorporated into the compositions of the present invention. The copolymer used in the present invention can be defined as being a derivative of vinylpyrrolidone, more precisely either a copolymer of polyvinylpyrrolidone (PVP) and α-olefins, or an alkylated derivative of polyvinylpyrrolidone. Optionally, these polymers are lipophilic.

These polymers can also be represented by the following formula:

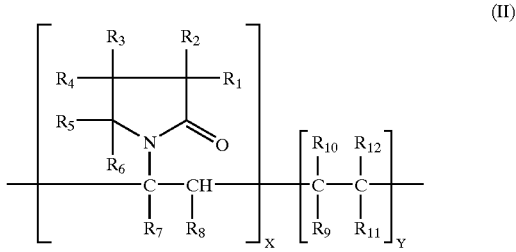

(II)

in which the radicals $R_1$–$R_{12}$ represent, independently of each other, a straight or branched $C_{10}$–$C_{40}$ alkyl radical, or a hydrogen atom, wherein at least one of said radicals $R_1$–$R_{12}$ being different from the hydrogen atom. The value Y can be equal to or greater than zero and X must not be equal to zero.

In one embodiment, the polymer used in the present invention contains at least one radical R comprising 14–32 carbon atoms, optionally 28–32 carbon atoms.

The alkyl radicals comprising 10–40 carbon atoms include pentadecyl, hexadecyl, heptadecyl, octadecyl, nonadecyl, eicosyl, docosyl, and tricontyl radicals.

In some embodiments of the present invention, the weight average molecular weight of the PVP copolymers range from about 5000 to about 30,000, optionally from about 6000 to about 20,000.

In a particular embodiment of the invention, Y equals 0 and the radicals $R_2$–$R_5$ represent hydrogen. Optionally, at least one of the different radicals of hydrogen comprises 14–32 carbon atoms. The polymers that satisfy this embodiment variant include tricontanyl PVP marketed by ISP under the tradename Ganex WP-660® and Antaron WP-660®.

In another embodiment of the invention, Y cannot equal zero. The radicals $R_1$–$R_9$ and $R_{11}$ and $R_{12}$ preferably represent hydrogen. Also, $R_{10}$ can comprise 14–32 carbon atoms, and, independently, an x/y ratio of 1/5-5/1.

Among the polymers included in this embodiment variant, one can mention the copolymer PVP/hexadecane or the copolymer PVP/eicosene marketed by ISP under the tradenames Ganex V-216® and Ganex V-220®, respectively. Ganex V-216® is a PVP/hexadecane copolymer comprising approximately 15–23% of pyrrolidone units with a weight average molecular weight of 7300. Ganex V-220® is a copolymer PVP/eicosene which comprises approximately 20–28% of pyrrolidone units and a weight average molecular weight of 8600.

The polymer according to the present invention has a consistency at ambient temperature that can present varying degrees of viscosity, depending on the length of the alkyl chain. Thus, it can be in liquid form with a viscosity on the order of 40–55 Poise (4–5.5 Pa-s) or in a more pasty form, or in a solid form having a consistency close to that of a wax.

The PVP copolymer can be present in the compositions of the present invention at a concentration of from about 0.05% to about 15%, optionally, from about 0.1% to about 10%, or from about 0.25% to about 5%, by weight of the composition. The abovementioned PVP copolymers of the present invention can be used alone or in combination.

Resin

The composition of the present invention may also comprise at least one resin. This resin is typically available from commercial manufacturers in the form of a water insoluble latex. Such latexes are aqueous emulsions or dispersions of polymeric materials or resins comprising polymers formed from monomers, said monomer derivatives, mixtures of said monomers, mixtures of said monomer derivatives, natural polymers and mixtures thereof. The resin also includes chemically modified versions of the above polymers. These compositions of the present invention comprise from about 0.1% to about 30%, preferably, from about 0.5% to about 25%, more preferably, from about 1% to about 10%, and most preferably, from about 2% to about 8%, by weight of the composition, of a resin. Additionally, the compositions of the present invention shall comprise no more than about 50%, by weight of the composition, of the latex, more preferably, from about 1% to about 40%, even more preferably from about 5% to about 20%, and most preferably, from about 10% to about 17%.

Water-insoluble latexes that comprise the requisite resin comprise monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols and mixtures thereof. In one embodiment, monomers are selected from the group consisting of aromatic vinyls, dienes, vinyl esters, olefins and their isomers, unsaturated carboxilic acids, alkyl esters of unsaturated carboxylic acids, hydroxy derivatives of alkyl esters of unsaturated carboxylic acids, amides of unsaturated carboxylic acids and mixtures thereof. In another embodiment, monomers are selected from the group consisting of aromatic vinyls, dienes, vinyl esters, alkyl esters of unsaturated carboxylic acids, hydroxy derivatives of alkyl esters of unsaturated carboxylic acids and mixtures thereof. The polymerization process for making the resin-containing latexes is well known in the art. Such processes are disclosed in Kirk Otimer, Encyclopedia of Chemical Technology, Volume 14, "Latex Technology" 3rd Ed. 1981; incorporated herein by reference.

Specific latexes useful in the present invention include, but, are not necessarily limited to the Syntran® Series (of latexes) from Interpolymer Corporation, for example Syntran 5170®, Polymer EX33-9, and Syntran 5130® (acrylates copolymers formulated with added ammonia, propylene glycol, preservative and surfactant) and Syntran 5002® (styrene/acrylates/methacrylate copolymer formulated with added ammonia, propylene glycol, preservative and surfactant); the Primal Series (acrylic latexes) from Rohm & Haas; Appretan V® (styrene/acrylic ester copolymer latexes) from Hoechst; Vinac® (polyvinylacetate latex) from Air Products; UCAR latex resin 130® (polyvinylacetate latex) from Union Carbide; Rhodopas A® Series (polyvinylacetate latexes) from Rhone Poulenc; Appretan MB, EM, TV® (vinyl acetate/ethylene copolymer latexes) from Hoechst; 200 Series (styrene/butadiene copolymer latexes) from Dow Chemical; Rhodopas SB® Series (styrenelbutadiene copolymer latexes) from Rhone Poulenc; Witcobond® (polyurethane latexes) from Witco; Hycar® Series (butadiene/acrylonitrile copolymer latexes) from Goodrich; Chemigum® Series (butadiene/acrylonitrile copolymer latexes) from Goodyear, and Neo Cryl® (styrene/acrylates/acrylonitrile copolymer latex) from ICI Resins. In preferred embodiments, the latex comprises an ammonium acrylates copolymer.

Waxes

When incorporated, waxes comprise the highest levels of solids in the composition of the present invention. Waxes are typically used at levels from about 1% to about 20%, optionally, from about 2% to about 18%, or from about 3% to about 15%, by weight of the composition.

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, synthetic waxes petroleum waxes, ethylenic polymers, hydrocarbon types such as Fischer-Tropsch waxes, silicone waxes, and mixtures thereof wherein the waxes have a melting point between 55° C. and 100° C. and a needle penetration, as measured according to the American standard ASTM D5, of 3 to 40 at 25° C. The principle of the measurement of the needle penetration according to the standards ASTM D5 consists of measuring the depth, expressed in tenths of a millimeter, to which a standard needle (weighing 2.5 g and placed in a needle holder weighing 47.5 g, i.e., a total of 50 g) penetrates when placed on the wax for 5 seconds.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); C24-45 alkyl methicones (silicone waxes); and mixtures thereof. Most preferred are beeswax, lanolin wax, carnauba, candelilla, ozokerite, ceresin, paraffins, microcrystalline waxes, polyethylene, C24-45 alkyl methicones, and mixtures thereof.

Fats

Fats are glyceryl esters of higher fatty acids such as stearic and palmitic. Such esters and their mixtures are solid at room temperature and exhibit crystalline structure. Fats are typically used at levels from about 5% to about 50%, preferably from about 10% to about 25% and most preferably from about 10% to about 20% by weight of the solids contained in the present invention.

The fats employed according to the invention are selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C. Preferably, the fats are selected from the group consisting of glyceryl monostearate, glyceryl distearate, glyceryl tristearate, palmitate esters of glycerol, C18-36 triglycerides, glyceryl tribehenate, C18-36 acid triglycerides and mixtures thereof.

In the present invention the phospholipid (e.g., lecithin) is at a level of at least 0.1%, by weight of the composition, and the ratio of fat (e.g., glycerol monostearate) to phospholipid is from about 2:1 to about 20:1, optionally from about 3:1 to about 12:1, or from about 3.5:1 to about 10.5:1.

Dermatologically Acceptable Carrier

Optionally, the compositions of the present invention contain a dermatologically acceptable carrier. The carrier can be volatile or nonvolatile. Suitable carriers are those that dissolve or uniformly disperse the components of the present invention. They include, but are not limited to, water, lower alcohols (such as ethanol, isopropanol), dihydric alcohols such as propylene and butylene glycol, polyols such as glycerin, hydroalcoholic mixtures, hydrocarbons (such as isobutane, hexane, decene, acetone), halogenated hydrocarbons (like Freon), linalool, hydrocarbon esters (such as ethyl acetate, dibutyl phthalate), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof. In one embodiment the carrier is selected from the group consisting of water, ethanol, volatile silicon derivatives, and mixtures thereof. Carriers, both volatile and non-volatile, useful in the present invention are further described in U.S. Pat. No. 5,750,096 to Gerald J. Guskey et al., issued May 12, 1998.

Pigments

The compositions of the present invention can, optionally, contain dermatologically-acceptable pigments selected from the group consisting of inorganic pigments, organic pigments, and organic lake pigments, pearlescent pigments, and mixtures thereof. When employed, the pigments are present in proportions depending on the color and the intensity of the color that it is intended to produce. The level of pigments in the solid portion of the composition is from about 3% to about 20%, preferably from about 5% to about 15%, and most preferably, from about 5% to about 10%. The pigments may optionally be surface-treated with treatments that include, but are not limited to, silicones, perfluorinated compounds, lecithin, and amino acids.

Inorganic pigments useful in the present invention include those selected from the group consisting of rutile titanium dioxide, anatase titanium dioxide (both coded in the Color Index under the reference Cl 77891); black, yellow and red iron oxides (Cl 77499, 77492 and 77491); bismuth oxychloride (Cl 77163); manganese violet (Cl 77742); ultramarines (Cl 77007); chromium oxide (Cl 77288); chromium hydroxide (Cl 77289); ferric ferrocyanide (Cl 77510); zinc oxide (Cl 77947); and mixtures thereof.

The organic pigments useful in the present invention include the dyes and the analogous lakes selected from the group consisting of D&C Red 6 (Cl 15850); D&C Red 7 (Cl 15850:1); D&C Red 21 (Cl 45380:2); D&C Red 22 (Cl 45380); D&C Red 27 (Cl 45410:1); D&C Red 28 (Cl 45410); D&C Red 30 (Cl 73360); D&C Red 33 (Cl 17200); D&C Red 34 (Cl 15880:1); D&C Red 36 (Cl 12085); D&C Orange 4 (Cl 15510); D&C Orange 5 (Cl 45370:1); D&C Orange 11 (Cl 45425); FD&C Yellow 5 (Cl 19140), FD&C Yellow 6 (Cl 15985); D&C Yellow 10 (Cl 47005); FD&C Green 3 (Cl 42053); D&C Green 5 (Cl 61570); FD&C Blue 1 (Cl 42090); Cochineal Carmine (Cl 75470); Guanine (Cl 75170) and mixtures thereof.

The pearlescent pigments useful in the present invention include those selected from the group consisting of mica (or a similar plate-like substrate) coated with any of the following materials alone or in combination: titanium dioxide, bismuth oxychloride, iron oxides, ferric ferrocyanide, chromium oxide, chromium hydroxide, and any organic pigment of the above-mentioned type and mixtures thereof.

Hydrophobic Conditioning Agents

The compositions of the present invention may optionally contain one or more hydrophobic conditioning agents. Preferably, the weighted arithmetic mean solubility parameter of the hydrophobic conditioning agent is less than or equal to 12. It is recognized, based on this mathematical definition of solubility parameters, that it is possible, for example, to achieve the required weighted arithmetic mean solubility parameter, i.e., less than or equal to 12, for a hydrophobic conditioning agent comprising two or more compounds if one of the compounds has an individual solubility parameter greater than 12.

Solubility parameters are well known to the formulation chemist of ordinary skill in the art and are routinely used as a guide for determining compatibilities and solubilities of materials in the formulation process.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$=the sum of the heat of vaporization additive group contributions, and $\sum_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974).

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977.

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp. 47–69.

Nonlimiting examples of hydrophobic conditioning agents include those selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). C7–C40 isoparaffins, a class of C7–C40 branched hydrocarbons, are useful herein. Polydecene, a branched liquid hydrocarbon, is also useful herein and is commercially available under the tradenames Puresyn 100® and Puresyn 3000® from Mobile Chemical (Edison, N.J.).

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, carpylic/capric triglyceride, PEG-6 caprylic/capric triglyceride, PEG-8 caprylic/capric triglyceride, and combinations thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810 ($C_{24}$–$C_{28}$ alkyl methicone) (sold by Goldschmidt) and SF1632 (cetearyl methicone)(sold by General Electric Company). Cyclomethicone/dimethicone copolyol mixtures are also particularly useful as formulation aid/conditioning agents. A suitable mixture is sold under the tradename DC 3225Q®.

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Hydrophobic chelating agents are also useful herein as hydrophobic conditioning agents. Suitable agents are described in U.S. Pat. No. 4,387,244, issued to Scanlon et al. on Jun. 7, 1983.

Preferred hydrophobic conditioning agents are selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkylarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Hydrophilic Conditioning Agents

The compositions of the present invention can also include one or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the articles of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990.

Structured Conditioning Agents

The compositions of the present invention may also include structured conditioning agents. Suitable structured conditioning agents include, but are not limited to, vesicular structures such as ceramides, liposomes, and the like.

Coacervates

The presently claimed compositions may also include cosmetic agents that are coacervate-forming. Preferably, the coacervate-forming cosmetic benefit agent comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

More preferably, the cationic polymer is selected from the group consisting of natural backbone quaternary ammonium polymers selected from the group consisting of Polyquaternium-4, Polyquaternium-10, Polyquaternium-24, PG-hydroxyethylcellulose alkyldimonium chlorides, guar hydroxypropyltrimonium chloride, hydroxypropylguar hydroxypropyltrimonium chloride, and combinations thereof; synthetic backbone quaternary ammonium polymers selected from the group consisting of Polyquaternium-2, Polyquaternium-6, Polyquaternium-7, Polyquaternium-11, Polyquaternium-16, Polyquaternium-17, Polyquaternium-18, Polyquaternium-28, Polyquaternium-32, Polyquaternium-37, Polyquaternium43, Polyquaternium-44, Polyquaternium-46, polymethacylamidopropyl trimonium chloride, acrylamidopropyl trimonium chloride/acrylamide copolymer, and combinations thereof; natural backbone amphoteric type polymers selected from the group consisting of chitosan, quaternized proteins, hydrolyzed proteins, and combinations thereof; synthetic backbone amphoteric type polymers selected from the group consisting of Polyquaternium-22, Polyquaternium-39, Polyquaternium-47, adipic acid/dimethylaminohydroxypropyl diethylenetriamine copolymer, polyvinylpyrrolidone/dimethylaminoethyl methacyrlate copolymer, vinylcaprolactam/polyvinylpyrrolidone/dimethylaminoethylmethacrylate copolymer, vinaylcaprolactam/polyvinylpyrrolidone/dimethylaminopropylmethacrylamide terpolymer, polyvinylpyrrolidone/dimethylaminopropylmethacrylamide copolymer, polyamine, and combinations thereof; and combinations thereof. Even more preferably, the cationic polymer is a synthetic backbone amphoteric type polymer. Even still more preferably, the cationic polymer is a polyamine.

When the cationic polymer is a polyamine, it is preferred that the cationic polyamine polymer be selected from the group consisting of polyethyleneimines, polyvinylamines, polypropyleneimines, polylysines and combinations thereof. Even more preferably, the cationic polyamine polymer is a polyethyleneimine.

In certain embodiments in which the cationic polymer is a polyamine, the polyamine may be hydrophobically or hydrophilically modified. In this instance, the cationic polyamine polymer is selected from the group consisting of benzylated polyamines, ethoxylated polyamines, propoxylated polyamines, alkylated polyamines, amidated polyamines, esterified polyamines and combinations thereof. The composition comprises from about 0.01% to about 20%, more preferably from about 0.05% to about 10%, and most preferably from about 0.1% to about 5%, by weight of the composition, of the cationic polymer.

Preferably, for the coacervate-forming cosmetic benefit agent, the anionic surfactant is selected from the group consisting of sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isethionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

Alternatively, the coacervate-forming cosmetic benefit agent may comprise an anionic polymer, a cationic surfactant, and a dermatologically acceptable carrier for the polymer and surfactant. The anionic polymer may be selected from the group consisting of polyacrylic acid polymers, polyacrylamide polymers, copolymers of acrylic acid, acrylamide, and other natural or synthetic polymers (e.g., polystyrene, polybutene, polyurethane, etc.), naturally derived gums, and combinations thereof. Suitable gums include alginates (e.g., propylene glycol alginate), pectins, chitosans (e.g., chitosan lactate), and modified gums (e.g., starch octenyl succinate), and combinations thereof. More preferably, the anionic polymer is selected from the group consisting of polyacrylic acid polymers, polyacrylamide polymers, pectins, chitosans, and combinations thereof. Suitable cationic surfactants include, but are not limited to, those discussed herein.

Vitamin Compounds

The present compositions may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

For instance, vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997) which is incorporated by reference herein in its entirety. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

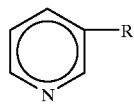

wherein R is —$CONH_2$ (i.e., niacinamide), —COOH (i.e., nicotinic acid) or —$CH_2OH$ (i.e., nicotinyl alcohol); derivatives thereof, and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

Anti-Acne Actives

Examples of useful anti-acne actives suitable for use in the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful in the cosmetic compositions of the present invention include, but are not limited to, retinoic acid and its derivatives (e.g., cis and trans); retinol; retinyl esters; niacinamide, and derivatives thereof; sulfur-containing D and L amino acids and their derivatives and salts, particularly the N-acetyl derivatives, a preferred example of which is N-acetyl-L-cysteine; thiols, e.g., ethane thiol; terpene alcohols (e.g., farnesol); hydroxy acids, phytic acid, lipoic acid; lysophosphatidic acid, alpha-hydroxy acids (e.g., lactic acid and glycolic acid), beta-hydroxy acids (e.g., salicylic acid), and skin peel agents (e.g., phenol and the like).

Enzymes

The compositions of the present invention may include one or more enzymes. Preferably, such enzymes are dermatologically acceptable. Suitable enzymes include, but are not limited to, keratinase, protease, amylase, subtilisin, other peptides and proteins, etc.

Peptides, including but not limited to, di-, tri-, tetra-, and pentapeptides and derivatives thereof, may be included as the cosmetic benefit agents of the present invention in amounts that are safe and effective. As used herein, "peptides" refers to both the naturally occuring peptides and synthesized peptides. Also useful herein are naturally occurring and commercially available compositions that contain peptides.

Sunscreen Actives

Also useful herein as cosmetic benefit agents are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Sagarin, et al., at Chapter VIII, pages 189 et seq., of *Cosmetics Science and Technology*. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema.

Chelators

The bonding agents of the present compositions may also include chelators as the cosmetic benefit agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably in amounts of from about 0.1% to about 10%, more preferably from about 1% to about 5%, by weight of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime, furildioxime derivatives, furilmonoxime, furilmonoxime derivatives, and combinations thereof.

Flavonoids

The compositions of the present invention may also include a flavonoid compound. Flavonoids are broadly disclosed in U.S. Pat. Nos. 5,686,082 and 5,686,367. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., a glycoside, an ester or an ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Sterols

Sterols may also be included in the presently claimed compositions. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The cosmetic compositions may also include an anti-cellulite agent. Suitable agents may include, but are not limited to, xanthine compounds (e.g., caffeine, theophylline, theobromine, and aminophylline), forskolin, and derivatives thereof.

Skin Lightening Agents

Another suitable cosmetic benefit agent that may be included in the present compositions is a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, deoxyarbutin, ascorbic acid and derivatives thereof, e.g., magnesium ascorbyl phosphate or sodium ascorbyl phosphate or other salts of ascorbyl phosphate.

EXAMPLES

The cosmetic products in the following examples illustrate specific embodiments of the cosmetic compositions of the present invention, but are not intended to be limiting thereof. Other modifications can be undertaken by the skilled artisan without departing from the spirit and scope of this invention. All exemplified compositions can be prepared by conventional formulation and mixing techniques. Component amounts are listed as weight percents and may exclude minor materials such as diluents, filler, and so forth. The listed formulations, therefore, comprise the listed components and any minor materials associated with such components.

Example #1

Long Wear Mascara

| Material | (w/w) % |
|---|---|
| Phase A: | |
| Glyceryl Monostearate[1] | 8.91 |
| $C_{18-36}$ Acid Triglyceride | 6.09 |
| White Beeswax | 3.25 |
| Lecithin[2] | 2.5 |
| Carnauba Wax | 2.0 |
| Tricontanyl PVP[3] | 3.0 |
| Stearic Acid | 3.4 |
| Potassium Cetyl Phosphate | 1.6 |
| Phase B: | |
| Deionized Water | 41.6 |
| Trisodium EDTA | 0.1 |
| Phase C: | |
| Micronized Black Pigment | 6.4 |
| Phase D: | |
| Simethicone | 0.2 |
| Phase E: | |
| Triethanolamine | 2.25 |
| Oleic Acid | 0.75 |

-continued

| Material | (w/w) % |
|---|---|
| Phase F: | |
| Ethyl Alcohol | 1.0 |
| Phenoxyethanol | 0.28 |
| Methylparaben | 0.25 |
| Ethylparaben | 0.25 |
| Benzyl Alcohol | 0.65 |
| Deionized Water | 1.02 |
| DL-Panthenol | 0.35 |
| Phase G: | |
| Ammonium Acrylates Copolymer[4] | 14.15 |

[1]Glycerol Monostearate available as Emerest 2400 from Henkel/Emery
[2]Lecithin available as Phospholipon 80 from American Lecithin
[3]Tricontanyl PVP available as Ganex WP-660 from ISP
[4]Ammonium Acrylates Copolymer available as Water Based Acrylates Copolymer Dispersion from Interpolymer Example #2

Thickening Mascara

| Material | (w/w) % |
|---|---|
| Phase A: | |
| Glyceryl Monostearate[1] | 6.35 |
| $C_{18-36}$ Acid Triglyceride | 4.15 |
| Lecithin[2] | 1.0 |
| PVP/Eicosene Copolymer[5] | 5.25 |
| Carnauba Wax | 2.25 |
| Propylparaben | 0.1 |
| Tricontanyl PVP[3] | 5.25 |
| Stearic Acid | 4.0 |
| Potassium Cetyl Phosphate | 1.0 |
| Phase B: | |
| Deionized Water | 43.67 |
| Trisodium EDTA | 0.1 |
| Phase C: | |
| Micronized Black Pigment | 6.0 |
| Phase D: | |
| Simethicone | 0.2 |
| Phase E: | |
| Triethanolamine | 2.0 |
| Oleic Acid | 1.0 |
| Phase F: | |
| Ethyl Alcohol | 1.0 |
| Phenoxyethanol | 0.28 |
| Methylparaben | 0.2 |
| Ethylparaben | 0.2 |
| Benzyl Alcohol | 0.65 |
| DL-Panthenol | 0.35 |
| Phase G: | |
| Ammonium Acrylates Copolymer[4] | 15.0 |

[1]Glycerol Monostearate available as Emerest 2400 from Henkel/Emery
[2]Lecithin available as Phospholipon 80 from American Lecithin
[3]Tricontanyl PVP available as Ganex WP-660 from ISP
[4]Ammonium Acrylates Copolymer available as Water Based Acrylates Copolymer Dispersion from Interpolymer
[5]PVP/Eicosene Copolymer available as Ganex V-220 from ISP Example #3

Long Wear Mascara

| Material | (w/w) % |
|---|---|
| Phase A: | |
| Glyceryl Monostearate[1] | 9.09 |
| $C_{18-36}$ Acid Triglyceride | 5.88 |
| White Beeswax | 3.48 |
| Lecithin[2] | 2.5 |
| Paraffin Wax | 2.41 |
| Carnauba Wax | 2.14 |
| Propylparaben | 0.1 |
| Tricontanyl PVP[3] | 1.6 |
| Stearic Acid | 4.0 |
| Potassium Cetyl Phosphate | 1.0 |
| Phase B: | |
| Deionized Water | 41.0 |
| Trisodium EDTA | 0.1 |
| Phase C: | |
| Micronized Black Pigment | 6.4 |
| Phase D: | |
| Simethicone | 0.2 |
| Phase E: | |
| Triethanolamine | 2.25 |
| Phase F: | |
| Ethyl Alcohol | 1.0 |
| Phenoxyethanol | 0.5 |
| Methylparaben | 0.2 |
| Ethylparaben | 0.2 |
| Benzyl Alcohol | 0.65 |
| Deionized Water | 0.87 |
| DL-Panthenol | 0.28 |
| Phase G: | |
| Ammonium Acrylates Copolymer[4] | 14.15 |

[1]Glycerol Monostearate available as Emerest 2400 from Henkel/Emery
[2]Lecithin available as Centrolex F from Central Soya.
[3]Tricontanyl PVP available as Ganex WP-660 from ISP
[4]Ammonium Acrylates Copolymer available as Water Based Acrylates Copolymer Dispersion from Interpolymer Mascara Method of Making:

Heat Phase A (wax phase) to 85° C. to 90° C. Once melting begins start low shear mixing. When Phase A is completely molten, add Phase C and homogenize for one hour. After one hour of homogenization, add Phase E. Once Phase E has been added, stop homogenizing and allow to mix for 30 minutes with moderate shear mixing. Simultaneously, heat Phase B (water phase) to 85° C. to 90° C. while applying low shear mixing. Once Phase B has reached 85° C. to 90° C., add Phase D and allow to mix for 15 minutes. Add water phase (Phases B and D) to the wax phase (Phases A, C, and E) and allow to emulsify for 45 minutes at 85° C. with moderate shear mixing. After emulsifying, begin cooling to 50° C. to 53° C. When the temperature reaches 50° C. to 53° C., add Phase F and maintain temperature for 30 minutes. After 30 minutes, cool to 47° C. and add Phase G and maintain temperature for 20 minutes. After 20 minute, cool to 40° C. and transfer to storage vessel.

Example #4

Lipstick

| Material | (w/w) % |
|---|---|
| Phase A: | |
| Octyl Palmitate | 11.24 |
| Isopropyl Palmitate | 4.8 |
| Quaternium-18 Hectorite | 1.0 |
| Diisopropyl Dimerate | 5 |
| Phase B: | |
| Propylene Carbonate | 0.33 |
| Phase C: | |
| Glycerin | 8.98 |
| Ammonium Acrylates Copolymer[3] | 2.5 |
| Phase D: | |
| Cetyl Recinolate | 1.0 |
| Octyl Methoxycinnamate | 7.25 |
| Ozokerite Wax | 6.75 |
| Candelilla Wax | 1.75 |
| Microcrystalline Wax | 0.75 |
| Tricontanyl PVP[2] | 2.5 |
| PG-3 Diisostearate | 10.05 |
| Lecithin[1] | 2.0 |
| Vitamin E Acetate | 0.5 |
| Propylparaben | 0.15 |
| Methylparaben | 0.15 |
| Benzoic Acid | 0.1 |
| Titanium Dioxide in Diisopropyl Dimerate | 5.0 |
| Phase E: | |
| Pearlescent Pigment* | 14.01 |
| Pigment* | 5.89 |
| Diisopropyl Dimerate | 8.25 |
| Phase F | |
| Ethylene Brassalate | 0.05 |

[1]Lecithin available as Phospholipon 80 from American Lecithin
[2]Tricontanyl PVP available as Ganex WP-660 from ISP
[3]Ammonium Acrylates Copolymer available as Water Based Acrylates Copolymer Dispersion from Interpolymer
*The composition, type and shade of the pigments and pearlescent pigments will vary depending on the shade of the lipstick. Pigments may come in solutions of Diisopropyl Dimerate Lipstick Method of Making:

Mix Phase A in beaker until solids are completely dissolved. When solids are dissolved, add Phase B and mix until Quaternium-18 Hectorite is activated (solution will noticeably increase in viscosity). Simultaneously, heat Phase C until solids are dissolved and then add Phase D. Combine Phases A, B, C, D and heat to 90° C. with moderate shear mixing. When combination appears homogenous, add Phase E and continue heating. Apply vacuum to mixture until air bubbles are removed and mixture is homogenous. Remove vacuum, add Phase F, and continue heating and mixing for 15 minutes. Transfer product to slimline mold and chill to 0° C.

Example #5

Eyeliner

| Material | (w/w) % |
|---|---|
| Phase A: | |
| Isoparaffin $C_{9-11}$ | 30.0 |
| Lanolin Acid | 6 |
| PVP/Eicosene Copolymer[2] | 2.4 |
| Carnuba Wax | 2.4 |
| Lecithin[1] | 1.9 |
| White Beeswax | 1.2 |
| Propylparaben | 0.1 |
| BHA | 0.05 |
| Phase B: | |
| Hydrophobic Black Pigment | 16.35 |
| Phase C: | |
| Deionized Water | 28.3 |
| Methylparaben | 0.35 |
| Sodium Dehydroacetate Monohydrate, NF | 0.3 |
| Trisodium EDTA | 0.05 |
| Phase D: | |
| Ammonium Hydroxide (27.5% Solution) | 0.6 |
| Phase E: | |
| Ammonium Acrylates Copolymer[3] | 10 |

[1]Lecithin available as Phospholipon 80 from American Lecithin
[2]PVP/Eicosene Copolymer available as Ganex V-220 from ISP
[3]Ammonium Acrylates Copolymer available as Water Based Acrylates Copolymer Dispersion Eyeliner Method of Making:

Heat Phase A to 80° C. with moderate shear mixing. Once all solids in Phase A have melted Add Phase B and begin homogenizing. Homogenize for one hour. After one hour take a sample and confirm a good pigment dispersion. Simultaneously, heat Phase C to 80° C. while applying moderate shear mixing. When Phase C has reached 80° C., add it to Phases A and B. Immediately after adding Phase C, add Phase D to the mixture, reduce homogenizer speed, and begin slow cooling to 57° C. When solution has reached 57° C., add Phase E and allow to mix for 20 minutes at current temperature. After 20 minutes, stop homogenizing and begin cooling to 28° C. When product reaches 28° C., transfer it to storage vessel.

Example #6

Liquid Foundation

| Material | (w/w) % |
|---|---|
| Phase A: | |
| Titanium Dioxide* | 8.0 |
| Iron Oxide* | 1.4 |
| Talc* | 4.0 |
| Lecithin[1] | 1.6 |
| Cyclomethicone | 21.5 |
| Cyclomethicone and Dimethicone Copolyol | 7.5 |
| Phase B: | |
| PVP/Hexadecene Copolymer[2] | 2.25 |
| Ammonium Acrylates Copolymer[3] | 7.05 |
| Deionized Water | 45.0 |
| Sodium Chloride | 1.0 |
| Methylparaben | 0.25 |
| Polysorbate 20 | 0.2 |
| Ethylparaben | 0.25 |

[1]Lecithin available as Phospholipon 80 from American Lecithin
[2]PVP/Hexadecene Copolymer available as Ganex V-216 from ISP
[3]Ammonium Acrylates Copolymer available as Water Based Acrylates Copolymer Dispersion from Interpolymer
*The composition of these ingredients will vary depending on the shade.

Liquid Foundation Methods of Making:

Heat Phase A to 85° C. while applying low shear mixing. Mix Phase A until it is completely homogeneous.

Simultaneously, mix Phase B until it is uniform after heating to 85° C. Combine Phases A and B and homogenize for 15 minutes. Cool to room temperature while applying low shear mixing. A colloid mill may be used on the resulting product to achieve a desired particle size (typically 0.4 to 4 microns).

What is claimed is:

1. A cosmetic composition wherein said composition exhibits a turning point stress of from about 650 Pa to about 1500 Pa and a high shear rate slope of less than about 0.5 Pa-s.

2. The cosmetic composition of claim 1 wherein said turning point stress is from about 750 Pa to about 1200 Pa.

3. The cosmetic composition of claim 1 wherein said turning point stress is from about 850 Pa to about 1000 Pa.

4. The cosmetic composition of claim 1 wherein said high shear rate slope is less than about 0.25 Pa-s.

5. The cosmetic composition of claim 1 wherein said high shear rate slope is less than 0.01 Pa-s.

6. The cosmetic composition of claim 1 wherein said composition comprises a non-aqeuous primary solvent.

7. The composition of claim 1 wherein said composition comprises an aqueous primary solvent.

8. A cosmetic composition wherein said composition exhibits a turning point stress of from about 750 Pa to about 1200 Pa and a high shear rate slope of less than about 0.25 Pa-s.

9. The cosmetic composition of claim 1 wherein said composition comprises from about 0.1% to about 5%, by weight of the composition, of a phospholipid having the formula

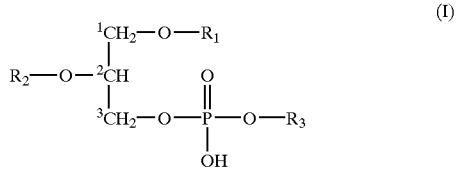
(I)

in which $R_1$ represent $C_{10-20}$ acyl, $R_2$ represent hydrogen or $C_{10-20}$ acyl, $R_3$ represent hydrogen, 2-trimethylamino-1-ethyl, 2-amino-1-ethyl, $C_{1-4}$ alkyl, $C_{1-5}$ alkyl substituted by carboxy, $C_{2-5}$ alkyl substituted by hydroxy, $C_{2-5}$ alkyl substituted by carboxy and hydroxy or $C_{2-5}$ alkyl substituted by carboxy and amino, the inositol group or the glyceryl group, or salts of these compounds.

10. The cosmetic composition of claim 1 wherein said composition comprises a dermatologically acceptable carrier.

11. The cosmetic composition of claim 10 wherein the carrier is a volatile carrier selected from the group consisting of water, lower alcohols, dihydric alcohols, polyols, hydroalcoholic mixtures, hydrocarbons, halogenated hydrocarbons, linalool, hydrocarbon esters, volatile silicones and mixtures thereof.

12. The cosmetic composition of claim 1 wherein said composition comprises a wax.

13. The cosmetic composition of claim 12 wherein the wax is selected from the group consisting of animal waxes, vegetable waxes, mineral waxes, various fractions of natural waxes, synthetic waxes, petroleum waxes, ethylenic polymers, Fischer-Tropsch waxes, silicone waxes, and mixtures thereof.

14. The cosmetic composition of claim 1 wherein said composition further comprises pigments selected from the group consisting of inorganic pigments, organic lake pigments, pearlescent pigments, and mixtures thereof.

15. The cosmetic composition of claim 1 wherein said composition is an emulsion.

16. The cosmetic composition of claim 15 wherein said composition is a water-in-oil emulsion.

17. The composition of claim 1 wherein said composition is in a product form suitable for application to keratinous tissue, said product form selected from the group consisting of lipsticks, foundations, eyeliners, lipliners, eyeshadows, rouges, and combinations thereof.

18. The composition of claim 1 wherein said composition is a mascara.

19. A cosmetic composition wherein said composition exhibits a turning point shear rate of from about 85 $s^{-1}$ to about 225 $s^{-1}$ and a high shear rate slope of less than about 0.5 Pa-s.

* * * * *